United States Patent
Fischer

(10) Patent No.: US 6,873,869 B2
(45) Date of Patent: Mar. 29, 2005

(54) METHOD AND APPARATUS FOR OBTAINING AN ELECTROCARDIOGRAPH

(75) Inventor: Roland Fischer, Wissembourg (FR)

(73) Assignee: Schiller Medical, Wissembourg (FR)

( * ) Notice: Subject to any disclaimer, the term of this patent is extended or adjusted under 35 U.S.C. 154(b) by 0 days.

(21) Appl. No.: 09/566,240

(22) Filed: May 5, 2000

(65) Prior Publication Data

US 2003/0114768 A1 Jun. 19, 2003

(30) Foreign Application Priority Data

May 7, 1999 (FR) .......................................... 99 05963

(51) Int. Cl.⁷ .............................................. A61B 5/04
(52) U.S. Cl. ...................................... 600/509; 128/901
(58) Field of Search ................................ 600/509, 508, 600/411, 413; 128/901

(56) References Cited

U.S. PATENT DOCUMENTS 4,593,702 A * 6/1986 Kepski ........................ 600/509
6,148,229 A * 11/2000 Morris, Sr. .................. 600/509

FOREIGN PATENT DOCUMENTS

EP 0 247 991 A 12/1987
FR 2 685 968 A 7/1993

* cited by examiner

Primary Examiner—Angela D. Sykes
Assistant Examiner—Roderick Bradford
(74) Attorney, Agent, or Firm—Davis & Bujold, P.L.L.C.

(57) ABSTRACT

A method of obtaining an electrocardiograph (ECG) of a patient located in a turbulent electromagnetic environment. The method includes recovering an ECG signal from a patient. The signal, including added noise, is recovered near the cardiac region as the differential signal resulting from signals delivered by two electrodes forming part of a first measurement loop. The signal further consists of simultaneously recovering from the patient a second measurement signal incorporating at least the noise, as a differential signal resulting from the signals delivered by two electrodes forming part of a second measurement loop distinct from the first measurement loop. Then, the second measurement signal is added or subtracted from the first noisy ECG signal, in real time. The second measurement signal is as a function of the polarity of the noise in the second signal relative to the noise in the first noisy ECG signal. The resulting signal is processed, converted, transmitted and displayed in real time representing the ECG essentially devoid of noise.

14 Claims, 4 Drawing Sheets

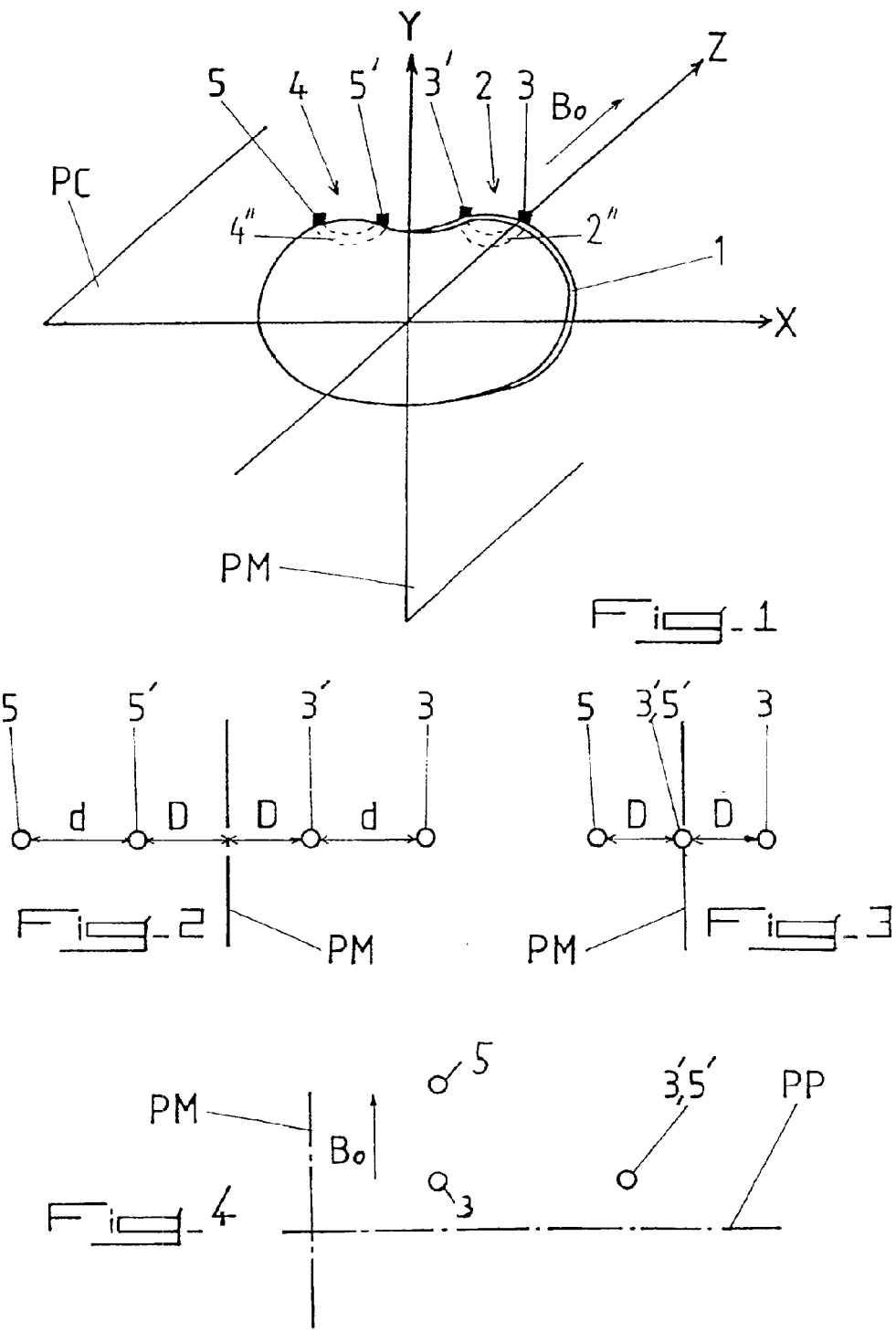

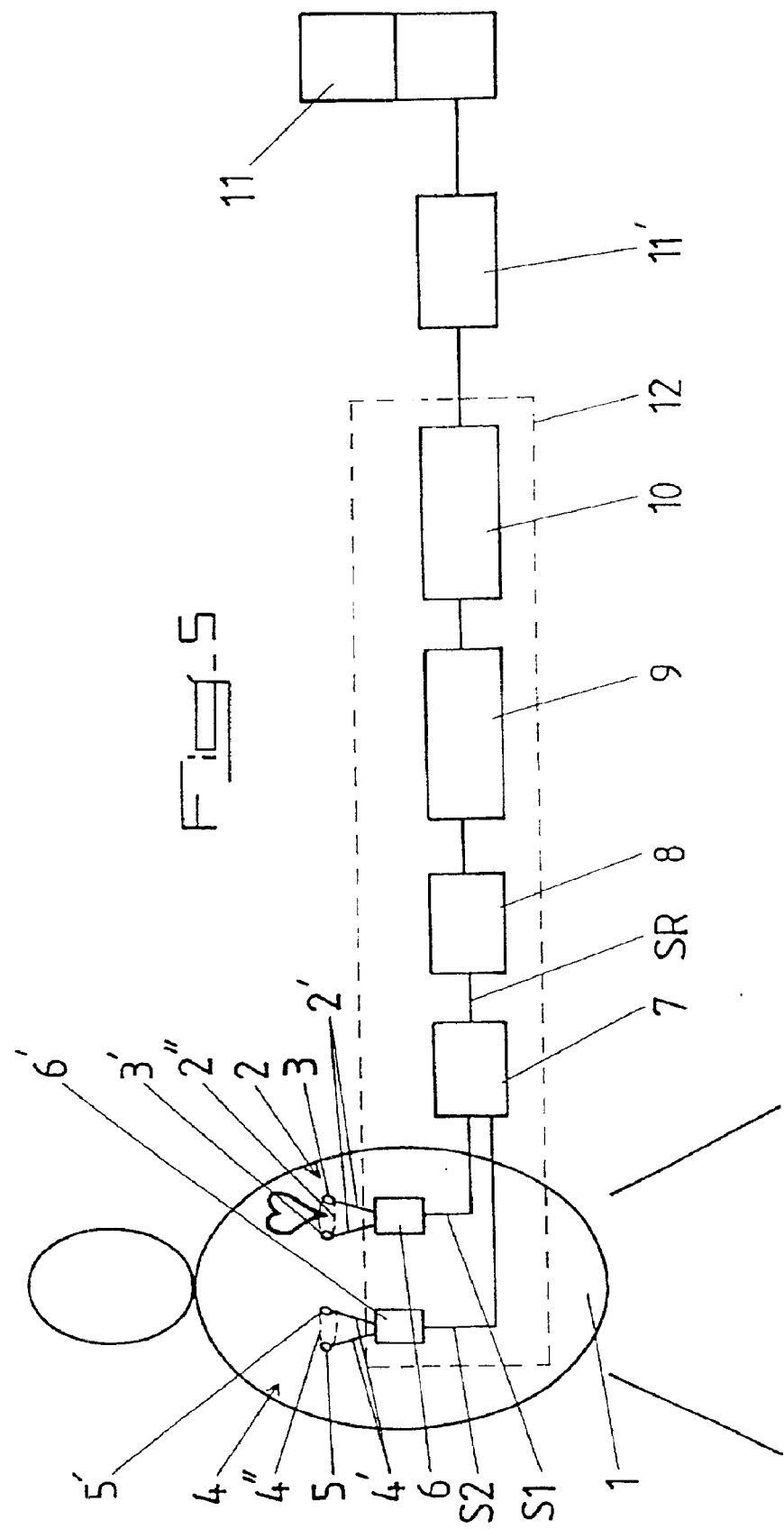

METHOD AND APPARATUS FOR OBTAINING AN ELECTROCARDIOGRAPH

The instant invention concerns obtaining and processing physiological signals, especially with a view toward improving the signal/noise relationship, and has as its object a method and a device for capturing an electrocardiograph signal (ECG) which is essentially devoid of noise, particularly noise caused by variations in the local magnetic field.

BACKGROUND OF THE INVENTION

In capturing physiological signals, obtaining a clear signal often poses a problem, as the signal is generally weak and drowned by background noise.

This difficulty increases when the signal is acquired in an MRI environment and when the signal involved is an electrocardiograph (ECG).

Not only is the electrocardiograph the preferred indicator of a patient's health, but it also serves as a sequencing signal, particularly for an MRI imager; for example, it may function as a signal for launching an acquisition sequence (better known as "triggering") and/or a signal for launching an acquisition window (better known as "gating").

In practice, the signal can be used in different ways, such as visualization, shape analysis, counting, or the like, in order to determine morphology, frequency, or other characteristics.

An electrocardiograph signal is a repetitive signal with each sequence consisting of a juxtaposition of several waves (P, QRS, T, ST).

Filtering signal noise is, of course, important in terms of monitoring. In actuality, in order to follow a patient's progress in real time, a doctor must have access to intelligible data; a noisy ECG is useless.

The detection of peaks in the QRS complex is of capital importance: first, in order to determine cardiac frequency, and second, to synchronize the capturing of images from an MRI imager with the ECG ("triggering"/"gating"). This cardiac synchronization allows each section to be excited at exactly the same moment in the cardiac cycle, and thus it provides an image of the section that is free of motion-related phenomena.

Currently the electrocardiograph signal-filtering phase is generally accomplished using analog circuits or dedicated chips with fixed characteristics and limited performances, which are not successful in effectively extricating the ECG signal from the artifacts and parasites arising from the electromagnetic turbulence that prevails, in particular, during MRI examinations.

These electromagnetic disturbances originate essentially from peaks and local changes in the principal magnetic field Bo from the action of gradients beginning during the MRI experience and introducing a noise signal in the measurement loop of the ECG signal, which may be equivalent in intensity or even louder than the ECG signal.

Note that Bo is oriented along the patient's longitudinal axis in the case of a tunnel MRI apparatus, and perpendicular to the patient's coronal plane in the case of an "open" type MRI apparatus.

Considering that the orientation of the principal field Bo corresponds to the axis Z of an orthogonal spatial index (X, Y, Z), the linear gradients at X, Y and Z can be represented as follows:

$$grad.X = \frac{dBz}{dx}, grad.Y = \frac{dBz}{dy} \text{ and } grad.Z = \frac{dBz}{dz}$$

In an attempt to suppress the noise signal induced, several solutions have been proposed.

For instance, it has been proposed to submit the ECG signal to a filter that is sensitive to the increasing voltage speed of the regulated signal at a value slightly higher than the typical maximum value of the dV/dt of the ECG.

However, this process does not suppress the noise induced by the application and suppression sequences of the different gradients of elevated frequency.

It has also been proposed to derive the acquired ECG signal into two secondary signals, to delay one of the latter signals for a duration corresponding to a multiple of the period of the ECG signal, to extract the noise component from it, and then perform a subtraction between the non-delayed signal and the noise component of a preceding period.

However, this method only leads to noteworthy improvement in the ECG signal if the induced noise, and thus the electromagnetic conditions, are essentially identical over several periods of the ECG signal and if the latter is relatively regular. In practice, this is not often true and a significantly distorted ECG signal may result.

The goal of the present invention is to overcome the difficulties enumerated above.

SUMMARY OF THE INVENTION

To achieve this, the object of invention is a method of obtaining the electrocardiograph (ECG) of a patient situated in a turbulent electromagnetic environment, consisting of obtaining an ECG signal from the patient including noise from the cardiac region, as well as a differential signal resulting from signals delivered by two electrodes forming part of a first measurement loop; and further consisting of simultaneously obtaining from the patient, in essentially identical turbulent conditions, a second measurement signal incorporating at least the noise, as a differential signal resulting from the signals delivered by two electrodes forming part of a second measurement loop distinct from the first; and then either adding to or subtracting from the first noisy ECG, in real time, the second measurement signal as a function of the noise polarity in the latter relative to the noise in the noisy ECG; and finally processing, converting, transmitting and/or displaying in real time the resulting signal which represents the ECG essentially devoid of noise.

The invention will be more readily understood with reference to the following description of some preferred embodiments cited as non-limitative examples, and explained in conjunction with the attached schematic drawings, wherein:

BRIEF DESCRIPTION OF THE DRAWING

FIG. 1 is a perspective of a transverse section of a patient, at the level of the heart, showing the implantation of electrodes according to a first variation of the method of the invention, particularly in relation to the principal field Bo in a tunnel MRI apparatus;

FIG. 2 is an overhead schematic view showing the arrangement of the electrodes of FIG. 1;

FIG. 3 is an overhead schematic view showing another electrode arrangement according to a second variation of the invention;

FIG. 4 is an overhead schematic view showing another electrode arrangement according to a third variation of the invention;

FIG. 5 is a block schema showing the different components of an ECG apparatus according to one particular realization of the invention;

DESCRIPTION OF THE PREFERRED EMBODIMENTS

Figure 6A:
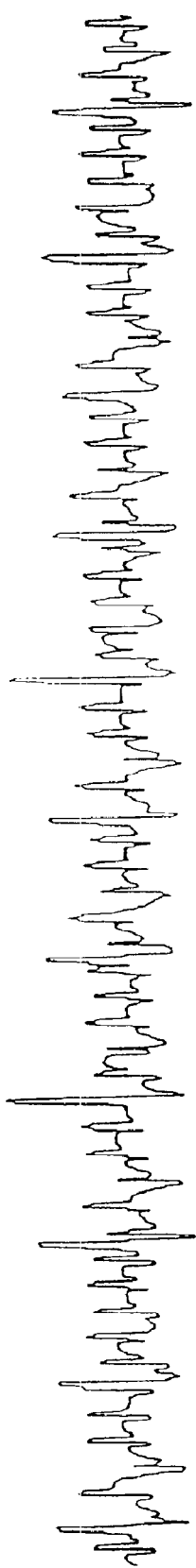
FIGS. 6A and 6B are temporal diagrams of electrocardiogram signals captured during the application of an MRI sequence with and without applying the method of the invention, respectively.

Thus, the method of acquiring the electrocardiograph (ECG) of a patient 1 situated in a turbulent electromagnetic environment consists, first, of recovering from patient 1 an ECG signal with additional noise S1 in the cardiac region as a differential signal resulting from the signals delivered by two electrodes 3, 3' forming part of a first measurement loop 2.

In accordance with the invention, said method further consists of recovering from patient 1, under essentially identical turbulent conditions, a second measurement signal S2 incorporating at least the noise, as a differential signal resulting from the signals delivered by two electrodes 5, 5' forming part of a second measurement loop 4 distinct from the first loop 2, then either adding to or subtracting from the first noisy ECG signal S1, in real time, said second measurement signal S2, as a function of the noise polarity in the latter signal relative to the noise in noisy ECG signal 1 and finally, processing, converting, transmitting, and/or displaying in real time the Resulting Signal SR, representing the ECG and essentially devoid of noise.

To ensure that at least one component representing the ECG is present in resulting signal SR, it is advantageous to provide that second measurement loop 4 is constituted and disposed so that if it acquires a signal component representing the ECG in addition to or mixed with the sound signal, said signal component representing the ECG has an opposite polarity and/or a smaller amplitude than the signal component representing the ECG recovered by first measurement loop 2.

Drawing inspiration from the creation and application of magnetic gradients during MRI experiments and the results of their cumulative actions in terms of creating and varying the intensity of local magnetic fields, the inventor has been able to determine which measurements to take in order to optimize reduction of the signal component relative to the noise induced by said gradients in the resulting ECG signal SR.

Thus, in the case of a patient 1 located in a nuclear magnetic resonance imager or a similar MRI apparatus, the apparent dimensions for magnetic flux in a plane PP perpendicular to the direction of the principal field Bo, of the first and second measurement loops 2 and 4 formed by connecting wires 2' and 4' of respective electrodes 3, 3' and 5, 5' and the material 2", 4" extending between the two electrodes 3, 3'; 5, 5" in a single measurement loop 4; 4 are determined to be similar, or even identical.

In the context of this application, the resulting signal SR could advantageously be used for surveillance and monitoring of a patient and to engage the magnetic resonance imager ("triggering" and/or "gating").

A comparison between FIGS. 1 and 2 of the attached drawings, as well as FIGS. 3 and 4, shows that depending upon the application and the constitution of the detection means used, the two measurement loops 2 and 4 could be physically separated and independent, or they could comprise a common electrode 3', 5'.

In accordance with a first embodiment of the invention, the first and second measurement loops 2 and 4 are disposed essentially symmetrically in relation to the median plane PM of patient 1 perpendicular to the patient's coronal plane PC, while electrodes 3, 3'; 5, 5' of the two measurement loops 2 and 4 are preferably, but not necessarily, arranged in alignment with similar spacing between the electrodes in each pair 3 and 3'; 5 and 5' (see FIGS. 1 through 3 and 5 of the attached drawings).

The inventor is able to state with certainty that the sound signals recovered by measurement loops 2 and 4 configured and arranged as described above are essentially identical in current MRI experiments making use of magnetic field gradients.

According to a second embodiment of the invention shown in FIG. 4 of the attached drawings, the three electrodes 3, 3'; 5, 5' forming the two measurement loops 2 and 4 are arranged in a triangular configuration near the cardiac region in such a way that the second measurement loop 4 recovers a signal component representing an ECG with opposite polarity and amplitude essentially equal to the signal component representing the ECG recovered by the first measurement loop 2.

Finally, so that it can be used in real time, especially to monitor the condition of a patient undergoing an MRI examination, the signal SR resulting from the addition or subtraction of the differential signals S1 and S2 delivered by the two measurement loops 2 and 4 can be processed by a pass-through filter 8, then used to modulate the frequency of a carrier and finally, transmitted to an apparatus 11 equipped with a means for displaying the filtered ECG signal SR, possibly after conversion into an optical signal.

It is also possible for the ECG signal to be ultimately submitted to numerical filtering using an infinite impulse response filter of the elliptical type, known as a Cauer filter, for example, a fourth order filter.

Yet another object of the present invention is an apparatus for acquiring an ECG signal in real time from a patient 1, particularly a patient undergoing an MRI examination, which can be connected to a display device 11, using the method described above.

This device consists principally of first, two modules 6, 6' for obtaining physiological signals S1 and S2 furnished by two distinct measurement loops 2 and 4, each comprising a pair of electrodes 3, 3'; 5, 5' placed on patient 1, with at least one of said two physiological signals S1, S2 comprising a component of a signal representing the ECG; and second, a module 7 which totals or differentiates signals S1 and S2 delivered by the two sampling modules 6, 6'; and finally, by modules 8, 9, 10, which process, or more specifically filter and convert signal SR furnished by said totaling or differentiating module 7.

Sampling modules 6, 6' advantageously each consist of a differential instrumentation amplifier with inputs connected to the respective electrodes.

Processing modules 8, 9, 10 may consist, respectively, of a pass-through filter 8 and a frequency modulation unit 9 and an electro-optic conversion module 10 connected to a fiber optic, the other end of which is connected to an opto-electronic conversion module 11' which is connected to or forms part of apparatus 11 incorporating the means for displaying the ECG signal.

Advantageously, all modules 6, 6', 7, 8, 9, 10 are grouped together in a protected housing 12 forming a Faraday cage which is connected to electrodes 3, 3'; 5, 5' with flexible, resistant connecting wires 2", 4" and which is not in direct contact with the patient's skin. Both sampling modules 6, 6' may also comprise a common electrode 3', 5'.

Moreover, the various elements and parts forming the apparatus of the invention can essentially consist of non-magnetic material, making it perfectly compatible with a magnetically sensitive, turbulent environment.

The apparatus implementing the acquisition method described above may consist of a sampling apparatus of the type described in French Patent No. 2 704 131 or in French Patent No. 2 729 071.

The advantages of the invention in terms of improved quality of the final ECG signal will be readily apparent from a study of FIGS. 6A, 6B, 7A and 7B of the attached drawings.

Figure 6B:

FIGS. 6A and 6B on the one hand, and 7A and 7B, on the other hand, represent electrocardiogram signals taken from the same patient, with the electrodes positioned in the same way and in the same electromagnetic environment.

Thus, the signals have been obtained with the electrodes placed at approximately 22 cm in front of the magnetic center, which constitutes the least favorable position (the point of maximum disruption due to gradient commutation), and with gradients of a magnitude of 16 mT/m.

Figure 7A:
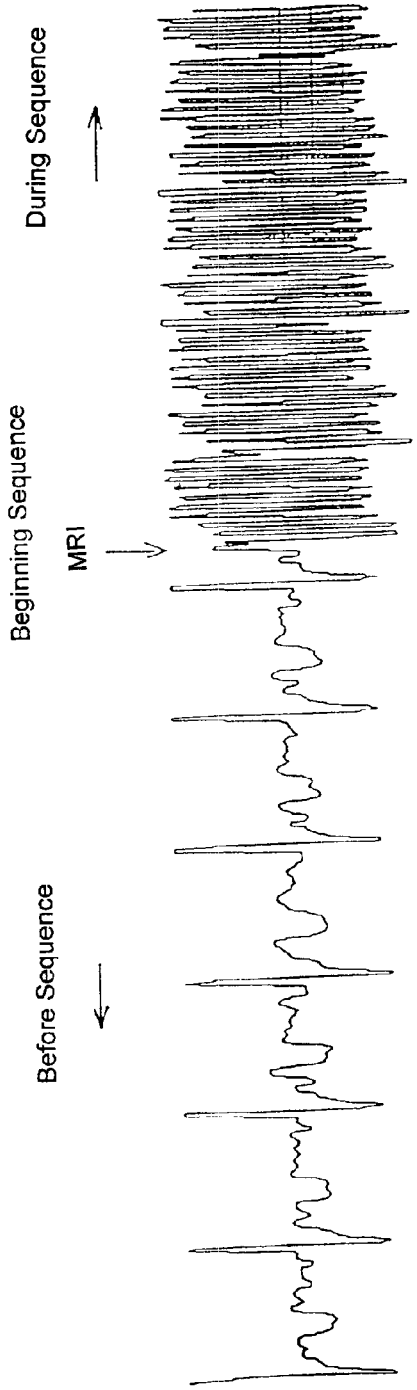
FIGS. 7A and 7B are also temporal diagrams of electrocardiogram signals captured before and during the application of an MRI sequence with and without applying the method of the invention, respectively.
Figure 7B:
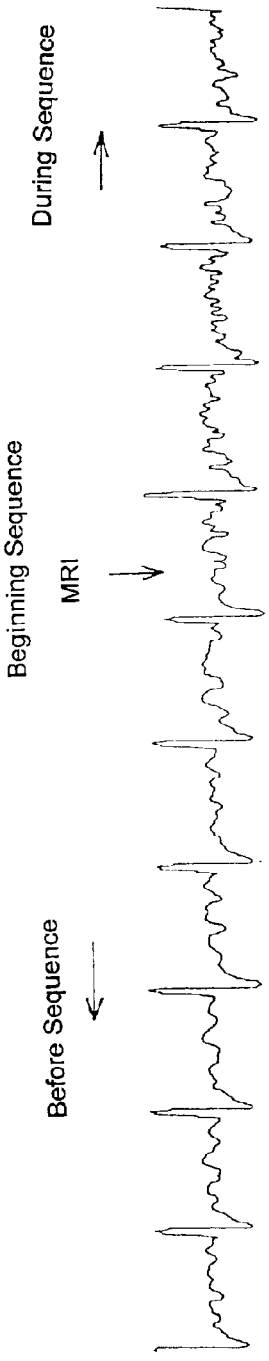

The signals in FIGS. 6A and 6B have been obtained during application of an MRI sequence of the type known as "Fast Spin Echo," while the signals in FIGS. 7A and 7B have been obtained before and during application of an MRI sequence of the type known as "Gradient Echo" with flux compensation.

The improvement in signal quality which results from applying the method of the invention will be clear from a comparison of FIG. 6A to FIG. 6B, and also FIG. 7A to FIG. 7B.

The invention remains valid even if the electrode arrangement is changed.

Obviously, the invention is not limited to the embodiments described and shown in the attached drawings. Various modifications are possible, particularly from the point of view of the constitution of the different elements, or the substitution of equivalent techniques, without departing from the scope of protection of the invention.

What is claimed is:

1. A method of obtaining an electrocardiograph of a patient under environment conditions in which the patient is also simultaneously undergoing at least one other procedure generating at least one other electromagnetic noise signal, the method comprising the steps of:
   subjecting the patient to the at least one other procedure generating the at least one other electromagnetic noise signal;
   dividing the patient lengthwise by a median plane;
   forming a first measurement circuit (2) consisting of a first pair of electrodes;
   forming a second measurement circuit (4) consisting of a second pair of electrodes;
   simultaneously obtaining an electrocardiograph signal (S1), including the electromagnetic noise signal, on a side of the median plane including the heart of the patient as a first differential signal measured across the first pair of electrodes;
   obtaining, under essentially identical environmental conditions, a second measurement signal (S2), including the electromagnetic noise signal, on an opposite side of the median plane remote from the heart of the patient as a second differential signal measured across the second pair of electrodes and is different from the first measurement circuit;
   one of adding and subtracting the second differential signal from the first differential signal, in real time, based on a polarity of the electromagnetic noise signal in the second measurement signal (S2) relative to the electromagnetic noise signal in the electrocardiograph signal (S1) to obtain a resulting signal (SR) substantially devoid of the electromagnetic noise signal; and
   processing and displaying, in real time, the resulting signal (SR) representing the electrocardiograph signal (S1).

2. The method of obtaining the electrocardiograph according to claim 1, further comprising the steps of detecting a secondary electrocardiograph signal in addition to or mixed with the second measurement signal including the other electromagnetic noise signal, and arranging the second measurement circuit (4) to obtain the secondary electrocardiograph signal having at least one of an opposite polarity and a lesser amplitude to the electrocardiograph signal (S1) obtained by the first measurement circuit (2).

3. The method of obtaining the electrocardiograph according to claim 1, further comprising the steps of situating the first and second pair of electrodes on the patient along a cornal plane such that a magnetic flux generated across the first pair of electrodes is substantially equal to a magnetic flux generated across the second pair of electrodes.

4. The method of obtaining the electrocardiograph according to claim 1, further comprising the step of forming the first and second measurement circuits (2 and 4) such that one of the first pair of electrodes and second pair of electrodes is an electrode (3', 5') common to both the first and second measurement circuits (2 and 4).

5. The method of obtaining the electrocardiograph according to claim 3, further comprising the step of arranging the first and second pair of electrodes essentially symmetrically relative to a median plane (PM) of the patient (1).

6. The method of obtaining the electrocardiograph according to claim 4, further comprising the step of arranging the first and second pair of electrodes essentially symmetrically relative to a median plane (PM) of the patient (1).

7. A method of obtaining an electrocardiograph of a patient under environment conditions in which the patient is also simultaneously undergoing a magnetic resonance imager process generating at least one other electromagnetic noise signal, the method comprising the steps of:
   subjecting the patient to the magnetic resonance imager generating the at least one other electromagnetic noise signal;
   dividing the patient lengthwise by a median plane;
   forming a first measurement circuit (2) consisting of a first pair of electrodes;
   forming a second measurement circuit (4) consisting of a second pair of electrodes, the first pair of electrodes being placed symmetrically, on the patient in relation to the median plane, with respect to the second pair of electrodes;
   simultaneously obtaining an electrocardiograph signal (S1), including the electromagnetic noise signal, on a side of the median plane including the heart of the patient, as a first differential signal measured across the first pair of electrodes;

obtaining, under essentially identical environmental conditions, a second measurement signal (S2), including the electromagnetic noise signal, on an opposite side of the median plane remote from the heart of the patient as a second differential signal measured across the second pair of electrodes and is different from the first measurement circuit;

subtracting the second differential signal from the first differential signal, in real time, based on a polarity of the electromagnetic noise signal in the second measurement signal (S2) relative to the electromagnetic noise signal in the electrocardiograph signal (S1) to obtain a resulting signal (SR) substantially devoid of the electromagnetic noise signal; and processing and displaying, in real time, the resulting signal (SR) representing the electrocardiograph signal (S1).

8. The method of obtaining the electrocardiograph according to claim 7, further comprising the steps of detecting a secondary electrocardiograph signal in addition to or mixed with the second measurement signal including the other electromagnetic noise signal, and arranging the second measurement circuit (4) to obtain the secondary electrocardiograph signal having at least one of an opposite polarity and a lesser amplitude to the electrocardiograph signal (S1) obtained by the first measurement circuit (2).

9. The method of obtaining the electrocardiograph according to claim 7, further comprising the steps of situating the first and second pair of electrodes on the patient along a cornal plane such that a magnetic flux generated across the first pair of electrodes is substantially equal to a magnetic flux generated across the second pair of electrodes.

10. The method of obtaining the electrocardiograph according to claim 7, further comprising the step of forming the first and second measurement circuits (2 and 4) such that one of the first pair of electrodes and second pair of electrodes is an electrode (3', 5') common to both the first and second measurement circuits (2 and 4).

11. A method of obtaining an electrocardiograph of a patient, using a maximum of four electrodes, under environment conditions which also the patient is also simultaneously undergoing a magnetic resonance imager process generating at least one other electromagnetic noise signal, the method comprising the steps of:

subjecting the patient to the magnetic resonance imager generating the at least one other electromagnetic noise signal;

dividing the patient lengthwise by a median plane;

forming a first measurement circuit (2) consisting of a first pair of electrodes;

forming a second measurement circuit (4) consisting of a second pair of electrodes, the first measurement circuit (2) being placed symmetrically, on the patient in relation to the median plane, with respect to the second measurement circuit (4);

while subjecting the patient to the at least one other procedure generating the at least one other electromagnetic noise signal, simultaneously obtaining an electrocardiograph signal (S1), including the electromagnetic noise signal, on a side of the median plane including the heart of the patient, as a first differential signal measured across the first pair of electrodes;

obtaining, under essentially identical environmental conditions, a second measurement signal (S2), including substantially only the electromagnetic noise signal, on an opposite side of the median plane remote from the heart of the patient as a second differential signal measured across only the second pair of electrodes and is different from the first measurement circuit;

subtracting the second differential signal from the first differential signal, in real time, based on a polarity of the electromagnetic noise signal in the second measurement signal (S2) relative to the electromagnetic noise signal in the electrocardiograph signal (S1) to obtain a resulting signal (SR) substantially devoid of the electromagnetic noise signal; and further processing in real time the resulting signal (SR) with one or more of a pass-through filter, a frequency modulation unit and an electro-optic conversion module connected by a fiber optic to an opto-electronic conversion module before displaying the resulting signal (SR).

12. The method of obtaining the electrocardiograph according to claim 11, further comprising the steps of detecting a secondary electrocardiograph signal in addition to or mixed with the second measurement signal including the other electromagnetic noise signal, and arranging the second measurement circuit (4) to obtain the secondary electrocardiograph signal having at least one of an opposite polarity and a lesser amplitude to the electrocardiograph signal (S1) obtained by the first measurement circuit (2).

13. The method of obtaining the electrocardiograph according to claim 11, further comprising the steps of situating the first and second pair of electrodes on the patient along a cornal plane such that a magnetic flux generated across the first pair of electrodes is substantially equal to a magnetic flux generated across the second pair of electrodes.

14. The method of obtaining the electrocardiograph according to claim 11, further comprising the step of forming the first and second measurement circuits (2 and 4) such that one of the first pair of electrodes and second pair of electrodes is an electrode (3', 5') common to both the first and second measurement circuits (2 and 4).

* * * * *